United States Patent
Hummel et al.

(10) Patent No.: US 7,195,900 B2
(45) Date of Patent: Mar. 27, 2007

(54) **CLONING AND EXPRESSION OF D-AMINO ACID OXIDASE FROM *ARTHROBACTER PROTOPHORMIAE***

(75) Inventors: Werner Hummel, Titz (DE); Birgit Geueke, Aachen (DE); Andrea Weckbecker, Aachen (DE); Klaus Huthmacher, Gelnhausen (DE); Christoph Weckbecker, Gründau (DE)

(73) Assignee: Degussa AG, Dusseldorf (DE)

( * ) Notice: Subject to any disclaimer, the term of this patent is extended or adjusted under 35 U.S.C. 154(b) by 420 days.

(21) Appl. No.: 10/463,868

(22) Filed: Jun. 18, 2003

(65) Prior Publication Data

US 2004/0009561 A1    Jan. 15, 2004

(30) Foreign Application Priority Data

Jun. 19, 2002    (DE)    ................ 102 27 493

(51) Int. Cl.
- C12N 9/02    (2006.01)
- C12N 1/20    (2006.01)
- C12N 15/00    (2006.01)
- C12P 21/04    (2006.01)
- C12Q 1/34    (2006.01)
- C07H 21/04    (2006.01)

(52) U.S. Cl. .................... 435/189; 435/69.1; 435/71.1; 435/440; 435/252.3; 435/320.1; 435/18; 536/23.2; 536/23.7

(58) Field of Classification Search ................ 435/189, 435/440, 252.3, 320.1, 69.1, 71.1, 18; 536/23.2, 536/23.7

See application file for complete search history.

(56) References Cited

U.S. PATENT DOCUMENTS

| 5,284,754 | A | 2/1994 | Bayer et al. .................. 435/47 |
| 6,187,574 | B1 | 2/2001 | Garcia Lopez et al. ..... 435/189 |
| 6,461,841 | B2 | 10/2002 | Geueke et al. .............. 435/136 |
| 2002/0106735 | A1 | 8/2002 | Geueke et al. .............. 435/106 |

FOREIGN PATENT DOCUMENTS

| EP | 0 897 006 A1 | 2/1999 |
| EP | 1 205 542 A1 | 5/2002 |
| WO | WO 96/27667 | 9/1996 |

OTHER PUBLICATIONS

English language abstract for EP 1 205 542, Reference AJ1 above.

Job, et al., "Overexpression of a Recombinant Wild-Type and His-Tagged *Bacillus subtilis* Glycine Oxidase in *Escherichia coli*," *Eur. J. Biochem.* 269:1456-1463 (2002).

Long-Liu, et al., "Expression of *Trigonopsis variabilis* D-amino Acid Oxidase Gene in *Escherichia coli* and Characterization of Its Inactive Mutants," *Enzyme and Microbial Technology* 27:482-491 (2000).

(Continued)

*Primary Examiner*—P. Achutamurthy
*Assistant Examiner*—Yong D. Pak
(74) *Attorney, Agent, or Firm*—Fitch, Even, Tabin & Flannery (57) ABSTRACT

The present invention is directed to a nucleotide sequence encoding D-amino oxidase (D-AAO, EC 1.4.3.3) from *Arthrobacter protophormiae*. This may be inserted into an expression and used to transform a microbial host. The transformed microbial hosts ecomically produce D-AAO which may be used to oxidize D-amino acids.

15 Claims, 4 Drawing Sheets

Different stages of purification of D-AAO

OTHER PUBLICATIONS

Databse EMBL 'Online! retrieved from EBI Database accession No. AJ000521 XP002253418.

Berg, et al., "Purification of D-Amino Acid Oxidase from *Trigonopsis variabilis*," *Analytical Biochem.* 71:214-222 (1976).

Butò, et al., "Evaluation of D-Amino Acid Oxidase from *Rhodotorula gracilis* for the Production of α-Keto Acids: A Reactor System," *Biotechnol. Bioeng.* 44:1288-1294 (1994).

Díez, et al., "Recombinant Microorganisms for Industrial Production of Antibiotics," *Biotechnol. Bioeng.* 55:216-226 (1997).

Fernández-Lafuente, et al., "The Coimmobilization of D-Amino Acid Oxidase and Catalase Enables the Quantitative Transformation of D-Amino Acids (D-Phenylalanine) into α-Keto Acids (Phenylpyruvic Acid)," *Enzyme Microbial Technol.* 23:28-33 (1998).

Fukunaga, et al., "Purification and Properties of D-Glutamate Oxidase from *Candida boidinii* 2201," *J. Ferment. Bioeng.* 85:579-583 (1998).

Gabler, et al., "Detection and Substrate Selectivity of New Microbial D-Amino Acid Oxidases," *Enzyme and Microbial Technol.* 27:605-611 (2000).

Hanson, et al., "Enzymatic Synthesis of L-6-Hydroxynorleucine," *Bioorg. Med. Chem.* 7:2247-2252 (1999).

Isogai, et al., "Structure and Expression of cDNA for D-Amino Acid Oxidase Active Against Cephalosporin C from *Fusarium solani*," *J. Biochem.* 108:1063-1069 (1990).

Jústiz, et al., "One-Pot Chemoenzymatic Synthesis of 3'-Functionalized Cephalosporines (Cefazolin) by Three Consecutive Biotransformations in Fully Aqueous Medium," *J. Org. Chem.* 62:9099-9106 (1997).

Koibuchi, et al., "Localization of D-Amino Acid Oxidase mRNA in the Mouse Kidney and the Effect of Testosterone Treatment," *Histochem. Cell Biol.* 104:349-355 (1995).

Konno, et al., "Guinea Pig D-Amino-Acid Oxidase cDNA and Phylogenetic Position," *DNA Seq.* 10:85-91 (1999).

Konno, "Rat D-Amino-Acid Oxidase cDNA: Rat D-Amino Acid Oxidase as an Intermediate Form Between Mouse and Other Mammalian D-Amino Acid Oxidases," *Biochim. Biophys. Acta* 1395:165-170 (1998).

Patel, "Enzymatic Synthesis of Chiral Intermediates for Omapatrilat, an Antihypertensive Drug," *Biomolec. Eng.* 17:167-182 (2001).

Sarkar, et al., "Screen-Printed Amperometric Biosensors for the Rapid Measurement of L- and D-Amino Acids," *Analyst* 124:865-870 (1999).

Sikora, et al., "Regulation of L-Amino Acid Oxidase and of D-Amino Acid Oxidase in *Neurospora crassa*," *Mol. Gen. Genet.* 186:33-39 (1982).

Simonetta, et al., "Purification and Properties of D-Amino-Acid Oxidase, an Inducible Flavoenzyme from *Rhodotorula gracilis*," *Biochim. Biophys. Acta* 914:136-142 (1987).

Váradi, et al., "Determination of the ratio of D- and L-Amino Acids in Brewing by an Immobilised Amino Acid Oxidase Enzyme Reactor Coupled to Amperometric Detection," *Biosensors & Bioelectronics* 14:335-340 (1999).

Yu, et al., "High Expressioin of *Trigonopsis variabilis* D-Amino Acid Oxidase in *Pichia pastoris*," *J. Molecular Catalysis B: Enzymatic* 18:291-297 (2002).

Wakayama, et al., "Isolation, Enzyme Production and Characterization of D-Aspartate Oxidase from *Fusarium sacchari* var. *elongatum* Y-105," *J. Ferment. Bioeng.* 78:377-379 (1994).

Figure 1

Different stages of purification of D-AAO

Figure 2: Effect of pH on enzyme activity

Figure 3: Plasmid pE1D

Figure 4: Temperature stability of homogenous D-AAO

CLONING AND EXPRESSION OF D-AMINO ACID OXIDASE FROM *ARTHROBACTER PROTOPHORMIAE*

CROSS REFERENCE TO RELATED APPLICATIONS

The present application claims priority to German application 102 27 493.2, filed on Jun. 19, 2002, which is incorporated in its entirety herein by reference.

Field of the Invention

The present invention is directed to a nucleotide sequence encoding D-amino oxidase (D-AAO) from *Arthrobacter protophormiae*. It includes expression vectors containing this sequence and host cells transformed with the vectors. The transformed microbial hosts may be used to economically produce D-AAO, an enzyme which oxidizes D-amino acids.

BACKGROUND OF THE INVENTION

D-amino acid oxidases (D-AAOs; EC 1.4.3.3) catalyze the oxidative deamination of D-amino acids to keto acids, accompanied by the liberation of ammonia and hydrogen peroxide. A cofactor of this reaction is FAD which is reoxidized by molecular oxygen to form $H_2O_2$.

Reaction equation of D-AAO

D-AAO activity was first detected in mammalian tissue in 1935 (Krebs, *Biochem. J.* 29:77–93 (1935)). In the following decades, D-AAOs from a variety of mammalian tissues, fish, birds and reptiles were reported (Konno, et al., *DNA Seq.* 10(2):85–91 (1999)); Konno, R., *Biochim. Biophys. Acta* 1395(2):165–170 (1998)); Koibuchi, et al., *Histochem. Cell Biol.* 104(5):349–55 (1995)); Konno, et al., *Zool Mag* (Tokyo), 90:368–73 (1981)).

With respect to microbial D-AAOs, studies have been largely limited to enzymes derived from eukaryotes. Microorganisms whose D-AAOs have been studied include yeasts *Rhodotorula gracilis* (Pilone, et al., *Biochim. Biophys. Acta* 914:136–142 (1987)), *Trigonopsis variabilis* (Berg, et al., *Anal. Biochem.* 71(1):214–22 (1976)) and several Candida species (Gabler, et al., *Enzyme Microbial Technol.* 27(8): 605–611 (2000)), and moulds *Neurospora crassa* (Sikora, et al., *Mol. Gen. Genet.* 186(1):33–9 (1982)), *Verticillium luteoalbo* and various Fusarium species (Gabler, et al., *Enzyme Microbial Technol.* 27(8):605–611 (2000); Isogai, et al., *J. Biochem.* (*Tokyo*) 108(6):1063–9 (1990)). The D-aspartate and D-glutamate oxidases are a special group of enzymes that exclusively oxidize acidic D-amino acids and derivatives thereof (Fukunaga, et al., *J. Ferment. Bioengineer.* 85(6):579–583 (1998)); Wakayama, et al., *J. Ferment. Bioengineer.* 5(5):377–379 (1994)).

The most important field of use of D-AAOs is in the preparation of 7-aminocephalosporanic acid (7-ACA), a starting material for the production of semi-synthetic β-lactam antibiotics (Justiz, et al., *J. Org. Chem.* 62:9099–9106 (1997); Diez, et al, *Biotechnol. Bioeng.* 55(1):216–226 (1996)). In this two-stage process, the amino group of the D-aminoadipyl side chain of cephalosporin C is oxidized by D-AAO and ketoadipyl-7-aminocephalosporanic acid is formed.

D-AAOs may also be used in the preparation of L-6-hydroxynorleucine, an intermediate for the antihypertensive agent omapatrilat (Hanson, et al., *Bioorg. Med. Chem.* 7(10):2247–52 (1999); Patel, *Biomol. Eng.* 17(6):167–82 (2001)) and as signallers in biosensors (Varadi, et al., *Biosens. Bioelectron.*, 14(3):335–40 (1999); Sarkar, et al., *The Analyst* 124:865–870 (1999)).

Another function of D-AAO is in the preparation of keto acids from D-amino acids. In this, the keto acid, i.e., the reaction product, must be protected from the $H_2O_2$ concurrently formed in order to prevent decarboxylation. By co-immobilization of catalase, both the decarboxylation of the keto acid by $H_2O_2$ and the oxidation of D-AAO itself are avoided (Buto, et al., *Biotechnol. Bioeng.* 44:1288–1294 (1994); Fernandez-Lafuente, et al., *Enzyme Microbial Technol.* 23:28–33 (1998)).

Practically all of the known D-AAOs have a limited spectrum of amino acids that they are capable of converting. A comparative overview of the substrates which can be used for six D-AAOs is provided by Gabler et al. (*Enzyme Microbial Technol* 27(8):605–611 (2000)). This reference reports that none of these enzymes are able to effectively utilize basic amino acids as substrates.

OBJECT OF THE INVENTION

The object of the invention is to provide a D-amino acid oxidase which is selective and which is able to efficiently use basic amino acids as substrates.

SUMMARY OF THE INVENTION

The present invention is based upon the cloning and sequencing of a D-amino acid oxidase gene from *Arthrobacter protophormia*. The gene codes for a form of D-amino acid oxidase that is effective in deaminating basic amino acids.

In its first aspect, the invention is directed to a protein having the amino acid sequence of SEQ ID NO:2 and which has D-amino acid oxidase activity. The sequence corresponds to that of the enzyme from *Arthrobacter protophormiae*. Preferably, the protein is at least 90% identical to SEQ ID NO:2 and maintains at least 90% of the D-amino acid oxidase activity of this protein. The D-AAO may be used to oxidatively deaminate D-amino acids, particularly basic D-amino acids, under conditions which promote the production of the corresponding keto acid. This process may be used as one step in the purification of enantiomers of the D-amino acids from a racemic mixture.

In another aspect, the invention is directed to an isolated polynucleotide encoding the D-amino acid oxidase described above. The sequence of this polynucleotide may be incorporated into a vector as a coding region. Preferably, the vector is an expression vector and the coding region is operably linked to a promoter. The invention includes host cells transformed with the vectors, with the most preferred host cells being those of the family Enterobacteriaceae and of the genus *Escherichia*. The transformed host cells may be used to produce the D-amino acid oxidase.

In another aspect, the invention is directed to an isolated polynucleotide that consists essentially of the nucleotide sequence of SEQ ID NO:1. The term "consists essentially of" or "consisting essentially of" is based both upon structural and functional considerations. Specifically, a "polynucleotide consisting essentially of the nucleotide sequence of SEQ ID NO:1" includes all polynucleotides that do not differ substantially in structure from SEQ ID NO:1. A substantial difference in structure would include any difference that results in a protein being encoded that differs significantly in D-AAO activity (e.g., by more than about 30%) relative to the protein of SEQ ID NO:2. Thus, differences in nucleotide sequence due to the degeneracy of the genetic code are within the scope of the term as are differences that result in the expression of an enzyme with an amino acid sequence different than SEQ ID NO:2 provided that the differences do not substantially alter enzymatic activity. In addition, the invention includes an isolated polynucleotide which hybridizes under stringent conditions to the complement (i.e., the complimentary sequence) of SEQ ID NO:1 and which encodes a protein having D-amino acid oxidase activity. Stringent conditions comprise washing in 5×SSC at a temperature of 50–68° C.

The invention includes vectors comprising a coding region corresponding to the isolated polynucleotide and, preferably, operably linked to a promoter. It also includes host cells transformed with the vector and methods of producing D-amino acid oxidase using the host cells. In all cases, the most preferred host cell is a bacterium of the family Enterobacteriaceae and of the genus *Escherichia*.

BRIEF DESCRIPTION OF THE FIGURES

FIG. 1: SDS/PAGE of D-AAO.

FIG. 2a: D-Methionine, FIG. 2b: D-Lysine, FIG. 2c: D-Phenylalanine. The enzyme activity was measured with three different substrates in the following 80 mM buffers: ♦ citric acid-sodium phosphate, pH 5–7; ■ TEA/HCl, pH 7–8.5; ▲ glycine/NaOH, pH 8.5–11. Each D-amino acid tested was employed in a final concentration of 10 mM.

DETAILED DESCRIPTION OF THE INVENTION

The present invention is based upon the isolation of a new gene from *Arthrobacter protophormiae* which codes for the enzyme D-amino acid oxidase (EC 1.4.3.3). One method in which isolation can be accomplished is to make and screen a gene library of *Arthrobacter protophormiae* in *Escherichia coli* (*E. coli*) using methods that are well known in the art (see e.g., Winnacker, *Gene und Klone, Eine Einführung in die Gentechnologie,* Verlag Chemie, Weinheim, Germany, (1990); or Sambrook, et al., *Molecular Cloning, A Laboratory Manual,* Cold Spring Harbor Laboratory Press, 1989). One well-known gene library is that of the *E. coli* K-12 strain W3110 made in λ vectors by Kohara et al. (*Cell* 50:495–508 (1987)). Bathe et al. (*Mol. Gen. Genetics* 252: 255–265 (1996)) describe a gene library of *C. glutamicum* ATCC13032, which was made with the aid of the cosmid vector SuperCos I (Wahl, et al., *Proc. Nat'l Acad. Sci. USA,* 84:2160–2164 (1987)) in the *E. coli* K-12 strain NM554 (Raleigh et al, *Nucl. Ac. Res.* 16:1563–1575 (1988)). Börmann et al. (*Mol. Microbiol.* 6(3):317–326 (1992)) describe a gene library of *C. glutamicum* ATCC13032 made using the cosmid pHC79 (Hohn, et al., *Gene* 11:291–298 (1980)). A gene library of *C. glutamicum* in *E. coli* may also be prepared using plasmids such as pBR322 (Bolivar, *Life Sciences* 25:807–818 (1979)) or pUC9 (Vieira, et al., *Gene* 19:259–268 (1982)).

Suitable hosts are, in particular, *E. coli* strains which are restriction- and recombination-defective, such as, for example, the strain DH5αmer, which has been described by Grant et al. (*Proc. Nat'l Acad. Sci. USA,* 87:4645–4649 (1990)). Using such strains, long DNA fragments can be cloned with the aid of cosmids or other λ vectors and subsequently sequenced in suitable vectors, e.g., those described by Sanger et al. (*Proc. Nat'l Acad. Sci. USA* 74:5463–5467 (1977)).

Instructions for identifying DNA sequences by means of hybridization can be found, inter alia, in the handbook "The DIG System Users Guide for Filter Hybridization" from Boehringer Mannheim GmbH (Mannheim, Germany, 1993) and in Liebl et al. (*Intern'l J. Systematic Bacteriol.* 41:255–260 (1991)). Probes can be constructed based upon the sequence information provided herein and hybridization should take place under stringent conditions such that the only hybrids obtained are those in which probe and annealed sequence are at least 70% identical. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approximately 50° C.–68° C., for example, can be employed for the hybridization reaction. Under these conditions, probes can also hybridize with polynucleotides that are less than 70% identical to the sequence of the probe. However, such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) and using a temperature of approximately 50° C.–68° C. Optionally, the salt concentration may be lowered even further, e.g., to 0.1×SSC. Polynucleotide fragments which are, for example, at least 70%, 80%, 90%, 95% or 99% identical to the sequence of the probe employed can be isolated by increasing the hybridization temperature stepwise from 50° C. to 68° C. in steps of approximately 1–2° C. It is also possible to isolate polynucleotide fragments which are completely identical to the sequence of the probe employed. Further instructions on hybridization are obtainable on the market in the form of so-called kits (e.g. DIG Easy Hyb from Roche Diagnostics GmbH, Mannheim, Germany, Catalogue No. 1603558).

Polynucleotides encoding D-AAO can also be obtained using the polymerase chain reaction (PCR). Instructions for amplification of DNA sequences with the aid of the PCR can be found, inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994). Suitable primers are described below.

One object of the present invention is to provide an expression construct containing at least one copy of a DNA sequence encoding D-amino acid oxidase operably linked to an appropriate regulatory region (e.g., a promoter). The expression construct may be inserted into a vector, preferably a plasmid, which is capable of transforming a microbial host cell and integrating into the genome.

It is also an object of the invention to provide a recombinant host which has been transformed by a vector as described in the preceding paragraph. Vector DNA can be introduced into prokaryotic or eukaryotic cells via conventional transformation or transfection techniques. As used herein, the terms "transformation" and "transfection," "conjugation" and "transduction" are intended to refer to a variety of art-recognized techniques for introducing foreign nucleic acid (e.g., linear DNA or RNA in the form of a linearized vector or a gene construct alone without a vector) or a nucleic acid in the form of an intact vector (e.g., a plasmid, phage, phasmid, phagemid, transposon or other DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells can be found in Sambrook, et al. (*Molecular Cloning: A Laboratory Manual*, $2^{nd}$, ed., Cold Spring Harbor Laboratory, Cold Spring Harbor Laboratory Press, Cold Spring Harbor, N.Y., 1989).

D-AAO-coding DNA sequences which result from the degeneracy of the genetic code are also a part of the invention. Conservative amino acid exchanges, such as e.g., exchange of glycine for alanine or aspartic acid for glutamic acid in proteins, are known in the art as "sense mutations" and generally do not lead to a fundamental change in the activity of the protein, i.e. they are of neutral function. Such mutations are also called, inter alia, neutral substitutions. Amino acid changes of this type that do not affect D-AAO activity are encompassed by the invention. Similarly, it is known that changes in the N and/or C terminus of a protein typically do not substantially impair, and can even stabilize, function. Information in this regard can be found, inter alia, in Ben-Bassat, et al. (*J. Bacteriol.* 169:751–757 (1987)), in O'Regan et al. (*Gene* 77:237–251 (1989)), in Sahin-Toth et al. (*Prot. Sci.* 3:240–247 (1994)), in Hochuli, et al. (*Bio/Technology* 6:1321–1325 (1988)) and in known textbooks of genetics and molecular biology.

DNA sequences which hybridize with SEQ ID NO:1 or parts of SEQ ID NO:1 are included within the invention as are DNA sequences which are prepared by the polymerase chain reaction (PCR) using primers derived from SEQ ID NO:1. Oligonucleotides obtained in this manner may be used as hybridization probes for RNA, cDNA and DNA, in order to isolate full length nucleic acids or polynucleotides or genes which code for D-amino acid oxidase or to isolate other nucleic acids or polynucleotides or genes which have a high degree of similarity with the dao gene. They are also suitable for incorporation into so-called "arrays," "micro arrays" or "DNA chips" in order to detect and determine the corresponding polynucleotides. In addition, the oligonucleotides are suitable for use as primers in PCR reactions performed to amplify DNA sequences coding for D-amino acid oxidases. The oligonucleotides should be at least 15 nucleotides in length and are preferably at least 20–30 nucleotides long. Oligonucleotides with lengths of 50, 100, 200, or 300 nucleotides can also be used.

It has been found that different microorganisms produce D-amino acid oxidase in an improved manner after enhancement of the of the D-AAO ("dao") gene of *Arthrobacter protophormiae*. The transformed microorganisms which can be used as hosts for the dao gene can produce the enzyme from glucose, sucrose, lactose, fructose, maltose, molasses, starch, cellulose or from glycerol and ethanol. These are fungi, yeasts or, preferably, Gram-positive bacteria or Gram-negative bacteria. The most preferred bacteria are of the Enterobacteriaceae and the genus *Escherichia*, with the species *Escherichia coli* being especially preferred.

The term "enhancement" in this connection describes an increase in the intracellular activity of one or more enzymes (proteins) in a recombinantly engineered microorganism relative to the same microorganism prior to engineering. This may be acomplished by, for example, increasing the number of copies of the relevant gene or allele, using a potent promoter or using a gene or allele which codes for a corresponding enzyme having a high activity. By enhancement measures, in particular over-expression, the activity or concentration of the corresponding protein can generally be increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism. The invention particularly includes bacteria in which there is an increased number of copies of the dao gene as the result of transforming the bacteria with the polynucleotide sequence of SEQ ID NO:1.

The D-amino acid oxidase of Arthrobacter can be produced by a process in which a recombinant microorganism, especially bacteria of the family Enterobacteriaceae which overexpress dao, are cultured under conditions conducive to the production of the dao gene product. The dao gene may comprise the nucleotide sequence of SEQ ID NO:1, any DNA sequence which results in the production of the same protein, or any sequence which has undergone trivial changes as evidenced by the expressed protein maintaining essentially all (for example at least 90%) of the D-amino acid oxidase enzymatic activity of the unmodified protein and a high degree of sequence homology (e.g., 90% or greater). The definition also includes any nucleotide sequence which hybridizes under stringent conditions to the complement of the nucleotide sequence of SEQ ID NO:1 and which encodes a polypeptide having D-amino acid oxidase activity. Stringent conditions include washing in 5×SSC at a temperature from 50 to 68° C. The D-amino acid oxidase produced is then enhanced in the cells of the microorganism being used for production or in the surrounding medium. For example, the amount of enzyme can be increased in bacterial cells by maintaining them in culture. The D-amino acid oxidase may then be isolated from the microorganism or the biological growth medium using standard techniques such as those described herein.

Provided that D-AAO activity is maintained, the polypeptides according to the invention may include a protein with a sequence identical to SEQ ID NO:2, or which is at least 70% to 80%, preferably at least 81% to 85%, particularly preferably at least 86% to 90% and very particularly preferably at least 91%, 93%, 95%, 97% or 99% identical.

Similarly, as long as polynucleotides meet the requirement of encoding the D-AAO protein as discussed herein they may be identical in sequence to SEQ ID NO:1 or be 70% to 80%, preferably at least 81% to 85%, particularly preferably at least 86% to 90% and very particularly preferably at least 91%, 93%, 95%, 97% or 99% identical.

The D-amino acid oxidase produced via the present invention may be applied to variety of processes which require the conversion of D-amino acids. For example, the D enantiomers of racemic mixtures can be deaminated and converted into the corresponding keto acids. Upon separation of these keto acids, the L content of the remaining mixture will be increased, i.e., enantiomer purity will be achieved or increased. The separation of keto acids from L-amino acids can be carried out by processes well known in the art, for example, by selective precipitation in acidic aqueous solution or by ion exchange chromatography. The purification of racemates chosen from the group consisting of the following amino acids is preferred: arginine, phenylalanine, ornithine, leucine, and histidine, and especially, methionine and lysine. The enzyme according to the invention has essentially an absolute enantiomer selectivity and is particularly well suited to the conversion of basic D-amino acids. These include, in particular: D-lysine, D-arginine and D-ornithine. However, apart from enantiomeric selectivity, the enzyme has a broad spectrum in terms of the particular amino acid that it utilizes as a substrate. Thus, many naturally occurring and non-naturally occurring amino acids can be converted.

The equilibrium of the reaction lies far on the right-hand side of the reaction equation, so that the reaction proceeds quantitatively. The reaction preferably includes FAD as a cofactor. External cofactor regeneration is, in general, not necessary, since the oxygen present regenerates the FAD spontaneously. The $H_2O_2$ formed in the reaction can be destroyed using procedures known in the art, e.g., with catalase.

The process is preferably carried out in an enzyme membrane reactor (see, DE 199 10 691). Enzymes can be used in the free form as homogeneously purified compounds or as enzymes prepared by a recombinant method. The enzymes can also be employed as a constituent of an intact guest organism or in combination with the broken-down cell mass of the host organism, purified to any desired extent. The use of the enzymes in immobilized form is also possible (Bhavender, et al., Angew. Chem. 94:836–852 (1982)). Immobilization is can be carried out by lyophilization (Dordick et al., J. Am. Chem. Soc. 116:5009–5010 (1994); Okahata, et al. Tetrahedron Lett. 38:1971–1974 (1997); Adlercreutz, et al., Biocatalysis 6:291–305 (1992)), preferably in the presence of a surface-active substance such as Aerosol OT, polyvinylpyrrolidone, polyethylene glycol (PEG) or Brij 52 (Goto et al., Biotechnol. Techniques 11:375–378 (1997)). Use as CLECs is also an option (St Clair, et al., Angew. Chem. Int Ed Engl. 39(2):380–383 (2000)).

Using the procedures described above, it has been found that, after the high cell density fermentation of E. coli BL21 (DE3) carrying pE1D (see Examples), D-AAO activity can reach 153,000 U liter$^{-1}$ in the fermentation broth. This value is much higher than values which have been published for the expression of recombinant and wild type D-AAOs. Also the specific activity in the crude extracts of recombinant cells (15–30 U mg$^{-1}$) exceeds data that has been published for known D-AAOs (Yu, et al, J. Mol. Catal. B: Enzymatic 18:291–297).

Definitions

The term "enantiomerically concentrated" describes the presence of one optical antipode as a mixture with the other in >50 mol %.

"Amino acid" in the context of the present invention is understood as meaning a naturally occurring or non-naturally occurring α- or β-amino acid, i.e. the radical on the α- or β-C atom of the α- or β-amino acid is derived from a naturally occurring amino acid, such as is described in Beyer-Walter, (Lehrbuch der organischen Chemie [Textbook of Organic Chemistry], S. Hirzel Verlag Stuttgart, 22nd edition, 1991, p. 822 et seq. (1991)), or from corresponding non-naturally occurring amino acids, (see, e.g., DE 199 03 268.8).

"Isolated" refers to a protein or polynucleotide that has been separated out of its natural environment and at least partly purified from other biological materials.

"Polynucleotide" refers to polyribonucleotides and polydeoxyribonucleotides. These may be non-modified RNA or DNA or RNA or DNA having modifications that are known in the art.

"Polypeptides" are understood as meaning peptides or proteins which comprise two or more amino acids bonded via peptide bonds.

The invention is illustrated in more detail in the following examples.

EXAMPLES

Example 1

Isolation and Characterization of *Arthrobacter protophormiae* D-217

To isolate D-AAO-forming microorganisms, soil samples were plated out on a nutrient medium in which coryneform bacteria can be concentrated: Na propionate 0.20 g; $KNO_3$ 0.01 g; $KH_2PO_4$ 0.10 g; NaCl 0.25 g; $MgSO_4.7 H_2O$ 0.10 g; $CaCO_3$ 0.02g; trace elements; vitamin solution; cyclohex-imide 0.05 g; if appropriate, agar 20.00 g; final pH 7.0. Microorganisms which grew on this medium were then transinoculated into a complex medium (DSM 65) with the following composition (per 1l): glucose 4.00 g; yeast extract 4.00 g; malt extract 10.00 g; agar 20 g; final pH 7.2. The strains were then multiplied in liquid medium (DSM 65), harvested by centrifugation, broken down, and the cell-free supernatant was obtained by centrifugation (=crude extract). This crude extract was then employed as an enzyme source for the photometric test for D-AAO activity. The test batch contained: 20 μl amino acid solution (100 mM); 80 μl TEA/o-dianisidine buffer; 10 μl peroxidase soln. (1,000 U/ml); 70 μl $H_2O$; 20 μl crude extract. The measurement was carried out at 436 nm; 1 U corresponds to an amount of enzyme which converts 1 μmol of amino acid or 1 μmol of o-dianisidine per min (extinction coefficient ε for o-dianisidine=8.1 mM$^{-1}$ cm$^{-1}$).

Screening gave a bacterium with intracellular D-AAO activity. This bacterium was determined to be a strain of *Arthrobacter protophormiae* with the following properties: It is strictly aerobic and Gram-positive—a catalase-positive rod-shaped organism which shows no formation of acid or gas from glucose. Neither a type of mobility nor the presence of spores is detected. The final assignment was rendered possible by sequencing of the 16S rDNA.

The strain *Arthrobacter protophormiae* designated as "ID99-1256" was deposited at the DSM under number 15035 on Apr. 6, 2002 at the Sammlung von Mikroorganismen und Zellkulturen GmbH in Braunschweig in accordance with the terms of the Budapest Treaty.

Example 2

High Cell Density Fermentation of *E. coli* BL21 (DE3) Carrying pE1D

A fed-batch fermentation was carried out using the following medium for the batch (per liter): 0.2 g NH$_4$Cl, 2 g (NH$_4$)SO$_4$, 13 g KH$_2$PO$_4$, 10 g K$_2$HPO$_4$, 6 g NaH$_2$PO$_4$.H$_2$O, 3 g yeast extract, 2 g glucose, 0.1 g ampicillin, 9.3 mg Na$_2$EDTA.2H$_2$O, 0.1 g thiamine, 0.3 ml antifoam, 5 ml vitamin and 4 ml trace element solution. The feed medium consisted of 0.2 g NH$_4$Cl, 2 g (NH$_4$)SO$_4$, 13 g KH$_2$PO$_4$, 10 g K$_2$HPO$_4$, 6 g NaH$_2$PO$_4$, 21 g yeast extract, 600 g glucose, 10 g MgSO$_4$.7H$_2$O, 0.4 ml antifoam, 5 ml vitamin solution and 2 ml trace element solution per liter. The vitamin solution contained (per liter): 0.1 g riboflavin, 10 g thiamine/HCl, 0.5 g nicotinic acid, 0.5 g pyridoxine/HCl, 0.5 g Ca-panthotenate, 1 mg biotin, 2 mg folic acid and 10 mg cyanocobalamin. The trace element solution contained (per liter): 10 g CaCl$_2$.H$_2$O, 0.5 g ZnSO$_4$.7H2O, 0.25 g CuCl$_2$.2H$_2$O, 2.5 g MnSO$_4$.H$_2$O, 1.75 g CoCl$_2$.6H$_2$O, 0.125g H$_3$BO$_3$, 2.5 g AlCl$_3$.6H$_2$O, 0.5 g Na$_2$MoO$_4$.2H$_2$O, 10 g FeSO$_4$.7H$_2$O.

The first preculture of *E. coli* BL21 (DE3) containing pE1D was inoculated in 5 ml LB$_{amp}$ medium from agar plates and cultivated for 14 h at 37° C. These cells were used for the inoculation of the second preculture consisting of 100 ml LB$_{amp}$ in a 500 ml Erlenmeyer flask. After 8 hours of incubation at 37° C., the preculture cells were used to inoculate the fermenter. Fermentation was carried out in a Techfors fermenter using the IRIS software (Infors, Bottmingen, Switzerland). The batch volume was 10 liter and the feed volume 5 liter. For the fed-batch fermentation, an exponential feeding strategy according to Korz et al. was slightly modified and applied according to the following equation (Korz, et al., *J. Biotechnol.* 39:59–65 (1995)).

$$m_S(t) = \left(\frac{\mu_{set}}{y_{X/S}} + m\right) \cdot V(t_0) \cdot X(t_0) \cdot e^{\mu_{set}(t-t_0)}$$

where $m_s$ is the mass flow of substrate (g h$^{-1}$), $y_{X/S}$ is the biomass/substrate yield coefficient (g g$^{-1}$), m the specific maintenance coefficient (g g$^{-1}$ h$^{-1}$), X the biomass concentration (g liter$^{-1}$) and V the cultivation volume (liter). The constant specific growth rate $\mu_{set}$ was set to 0.12 h$^{-1}$ to avoid accumulation of acetate. The cells were induced with 5 mM IPTG after 28 h of cultivation. The pO$_2$ was adjusted to 30% by adapting the stirrer speed, the pressure and the aeration rate. The pH was maintained at 7 by adding NH$_4$OH and the temperature was kept at 30° C. The cells were harvested with a separator KA06 (Westfalia, Oelde, Germany) after a fermentation time of 39 h.

After the high cell density fermentation of *E. coli* BL21 (DE3) carrying pE1D, 1.9 kg of cells (wet weight) were harvested which had an activity of 1200 U g$^{-1}$ cells (wet weight). The specific activity was 15 U mg$^{-1}$. We obtained 2.29 mill. units D-AAO from one 15 liter-fermentation.

Example 3

Purification of D-AAO

A. Purification from *Arthrobacter Protophormiae* D-217

It was possible to obtain homogeneous D-AAO by a three-stage purification. After two chromatography purification steps, the active fractions were combined, dialyzed and purified further by means of preparative, native gel electrophoresis. The yield was 8.5% and the D-AAO was concentrated 62-fold.

B. Purification of Recombinant D-AAO

Recombinant D-AAO was purified to homogeneity using a two-step procedure (Table 1). *E. coli* BL21(DE3) carrying pApdao was disrupted by ultrasonification and cell debris was removed by centrifugation. The cleared supernatant was loaded onto a Q-Sepharose FF column (h 10 cm×Ø 2.6 cm) (Amersham Bioscience), which was equilibrated with 10 mM potassium phosphate buffer pH 7.0 and run at a flow rate of 2 ml/min. The column was washed with 10 mM potassium phosphate buffer pH 7.0 containing 0.2 M NaCl and the D-AAO was eluted by increasing the salt concentration up to 0.35 M. Active fractions were pooled and loaded onto a column, which was packed with ceramic MacroPrep hydroxyapatite, type I (h 8.3 cm×Ø 1.6 cm) (Bio-Rad). The column was equilibrated with 10 mM potassium phosphate buffer pH 6.8 containing 150 mM NaCl and the flow rate was 2 ml/min. The D-AAO was detected in the flow-through.

Figure 1:
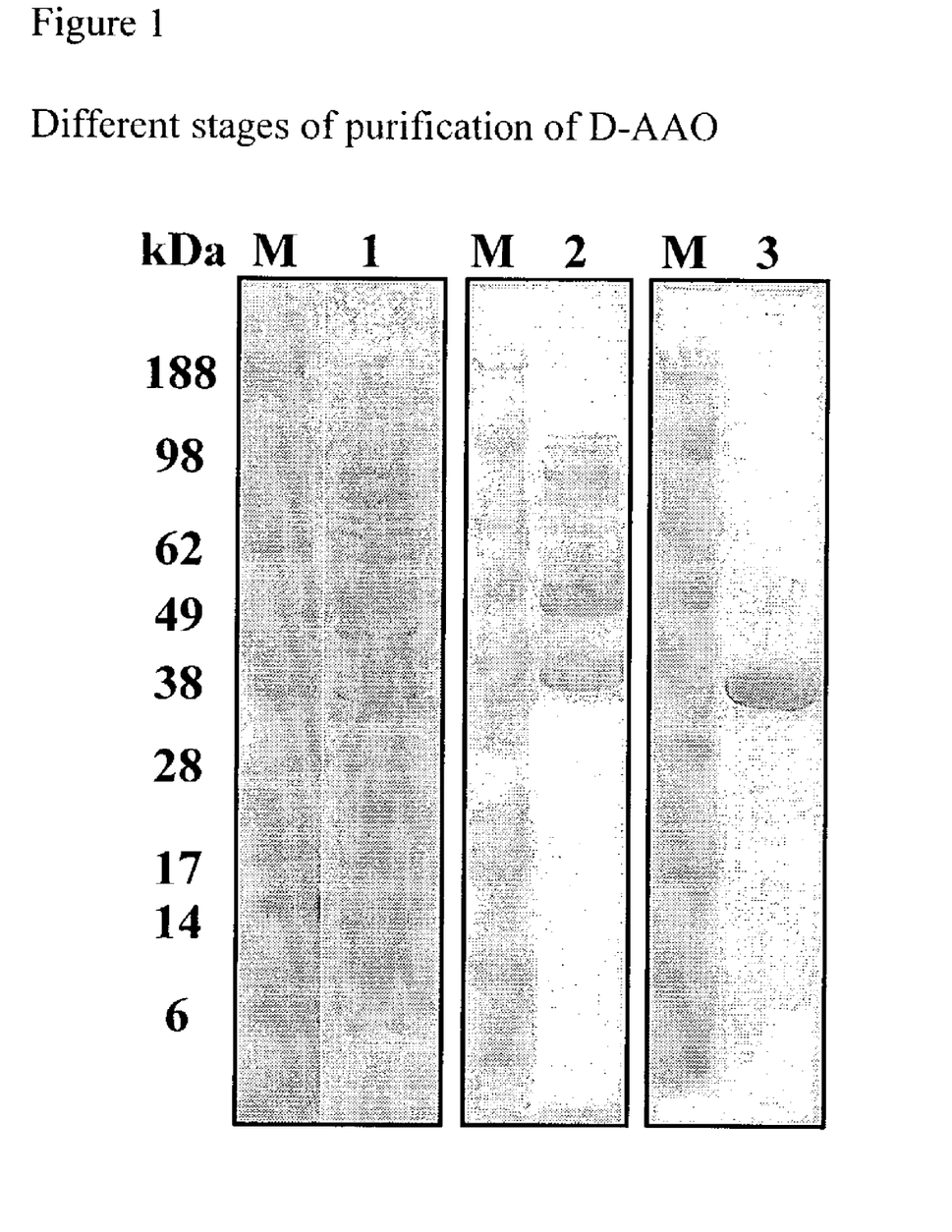
FIG. 1 shows samples at different stages of purification from *E. coli* BL21(DE3), and corresponding to Table 1. Lane M, marker; lane 1, crude cell extract; lane 2, pool after anion exchange chromatography; lane 3, pool after hydroxyapatite chromatography.

The specific activity of 30 U/mg in the crude extract could be increased six-fold to 180 U/mg after the second chromatography. We obtained 1434 U D-AAO from 3 g of cells (wet weight), which corresponds to 56% of the activity in the crude extract. The purification process was monitored by SDS/PAGE (FIG. 1).

TABLE 1

Purification scheme of D-AAO from *E. coli* BL21(DE3) (3 g cells, wet weight)

| | Total activity[n] [U] | Total protein [mg] | Volume [ml] | Specific activity [U/mg] | Purification [-fold] | Yield [%] |
|---|---|---|---|---|---|---|
| Crude extract | 2556 | 85 | 10 | 30 | 1.0 | 100 |
| Q-Sepharose | 1909 | 24 | 9.7 | 80 | 2.7 | 75 |
| Hydroxyapatite | 1434 | 8 | 12 | 180 | 6.0 | 56 |

[n]Activity assay: 0.2 M TEA/HCl, 10 mM D-Met, 100 U/ml peroxidase, 0.2 mg/ml o-dianisidine, D-AAO, pH 7.6, 30° C., 436 nm.

Example 4

Biochemical Characterization

A. Optimum pH

Figure 2:
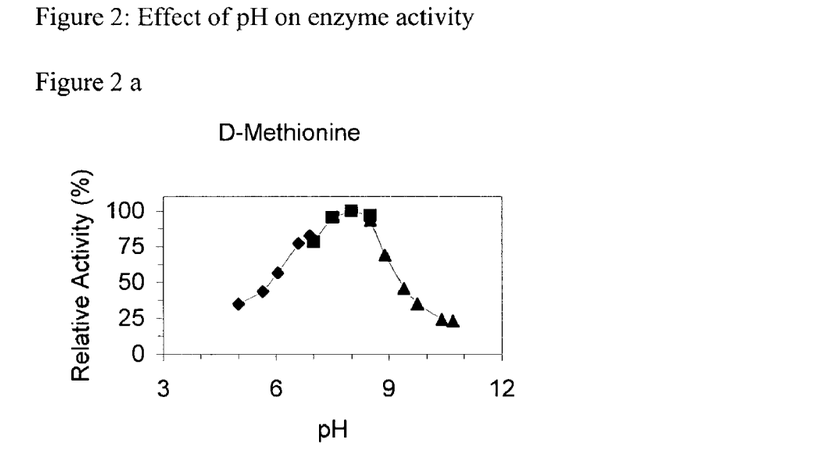
FIG. 2: Effect of the pH on the D-AAO activity.

The influence of pH on the activity of the D-AAO with respect to the substrates L-lysine, L-phenylalanine and L-methionine was investigated in three different buffers:

citric acid-sodium phosphate pH 4–7; TEA/HCl pH 7.0–8.5; and glycine/NaOH pH 8.5–11). The optimum pH for all three substrates was in the weakly basic range, between pH 7.5–8.5 (FIG. 2). The buffers employed did not substantially influence enzyme activity.

B. Substrate Spectrum

A partial substrate spectrum was recorded for D-AAO (Table 2). The best substrates were D-methionine and D-lysine. However, the enzyme was also effective in converting other substrates including D-phenylalanine, D-phenylalanine derivatives, and D-arginine.

The stereoselectivity of the D-AAO was tested with the amino acids L-leucine, L-methionine and L-lysine. None of these compounds were converted. Thus, the D-AAO from *Arthrobacter protophormiae* can be described as highly stereoselective for D-amino acids.

The kinetic constants for the substrates D-methionine and D-phenylalanine were determined with partly purified D-AAO. D-methionine, with a $K_M$ value of 0.90 mM, had a significantly higher affinity for the D-AAO than D-phenylalanine, the $K_M$ value of which was 16 mM. A substrate excess inhibition was moreover observed for D-phenylalanine ($K_I$=55 mM).

TABLE 2

Substrate specificity of the recombinant D-AAO

| Substrate | Relative activity [%][n] |
|---|---|
| D-Methionine | 100 |
| D-Lysine | 99 |
| 4-Fluoro-DL-phenylalanine | 81 |
| D-Arginine | 80 |
| D-Phenylalanine | 54 |
| DL-Homophenylalanine[#] | 31 |
| D-Ornithine | 15 |
| D-Leucine | 12 |
| D-Histidine | 5.9 |
| D-Tyrosine[#] | 4.7 |
| N-Methyl-DL-leucine | 2.1 |
| D-allo-Isoleucine | 1.0 |
| D-Valine | 0.35 |
| O-Methyl-DL-serine | 0.33 |
| D-Alanine | 0.26 |
| D-Proline | 0.25 |
| DL-tert-Leucine | 0.12 |

[n]The activities were measured with a final substrate concentration of 10 mM. In case DL-amino acids were used, the concentration was increased to 20 mM.
[#]300 µl of the supernatant of a saturated substrate solution were used in 1 ml assay volume for amino acid with low solubilities.

Example 5

Protein Chemistry Characterization

A. Molecular Mass and pI

A molecular mass for a monomer of the D-AAO of 40 kDA was determined by means of SDS gel electrophoresis. The native molecular mass was found to be 69 kDa after gel filtration. The calculated molecular mass of the monomer was 34.6 kDa without and 35.4 kDa with FAD. These values indicate that the enzyme has a dimeric structure. Isoelectric focussing was performed using precast Serva polyacrylamide gels with a narrow pH range (pH 4–6). The experimentally determined pI was 4.4.

B. Gene and Protein Sequence Data of the D-AAO

The first 20 amino acids of the protein were determined by automated Edman degradation of the N-terminus of the purified D-AAO after transfer to a PVDF membrane. The sequence of the N-terminus was found to be:

5'- PTAPLRITVIGSGVIGLSAA-3' (SEQ ID NO:3)

which corresponds to Pro Thr Ala Pro Leu Arg Ile Thr Val Ile Gly Ser Gly Val Ile Gly Leu Ser Ala Ala.

A further internal sequence was identified after proteolytic cleavage of the protein and separation of the peptides. The sequence was as follows:

Internal sequence 1: 5'-(K)LVPELEGLEVLEHK-3' (SEQ ID NO:4)

which corresponds to (Lys) Leu Val Pro Glu Leu Glu Gly Leu Glu Val Leu Glu His Lys.

Primers were constructed based on the N-terminal sequence information (SEQ ID NO:3) and the internal sequence information (SEQ ID NO:4). 75% of the gene sequence was amplified using this primer pair. The complete dao gene sequence was then isolated with the Universal GenomeWalker™ Kit (BD Clontech). Genomic DNA was cut with six restriction endonucleases NruI, EcoRV, PvuII, StuI, NaeI and FspI (BD Clontech or New England Biolabs). The GenomeWalker adaptors were ligated to the genomic DNA fragments and these libraries were used as templates in PCR reactions. Four primers were designed for the nested PCRs:

```
Apfor3:
5'-gcaccaggtcaccgtcgcctacgacca-3'     (SEQ ID NO:5)

Aprev3:
5'-caccagcttggcagcgcgttccagga-3'      (SEQ ID NO:6)

Apfor4:
5'-cgccgccgccatctggttcccgtacca-3'     (SEQ ID NO:7)

Aprev4:
5'-ctgcggttcgacttcgcggttccagtcgtt-3'. (SEQ ID NO:8)
```

The amplification procedures consisted of 3 min at 94° C. followed by 4 cycles of 1 min at 94° C., 30 s at 65° C., 3 min at 72° C., 30 cycles of 1 min at 94° C., 30 sec at 62° C. and 3 min at 72° C. The reaction was stopped after a final incubation step for 10 min at 72° C. The PCR products were analysed on agarose gel and used for direct sequencing. The gene sequence and the deduced protein sequence are found in the attached Sequence Listing.

Example 6

Cloning and Expression

Figure 3:
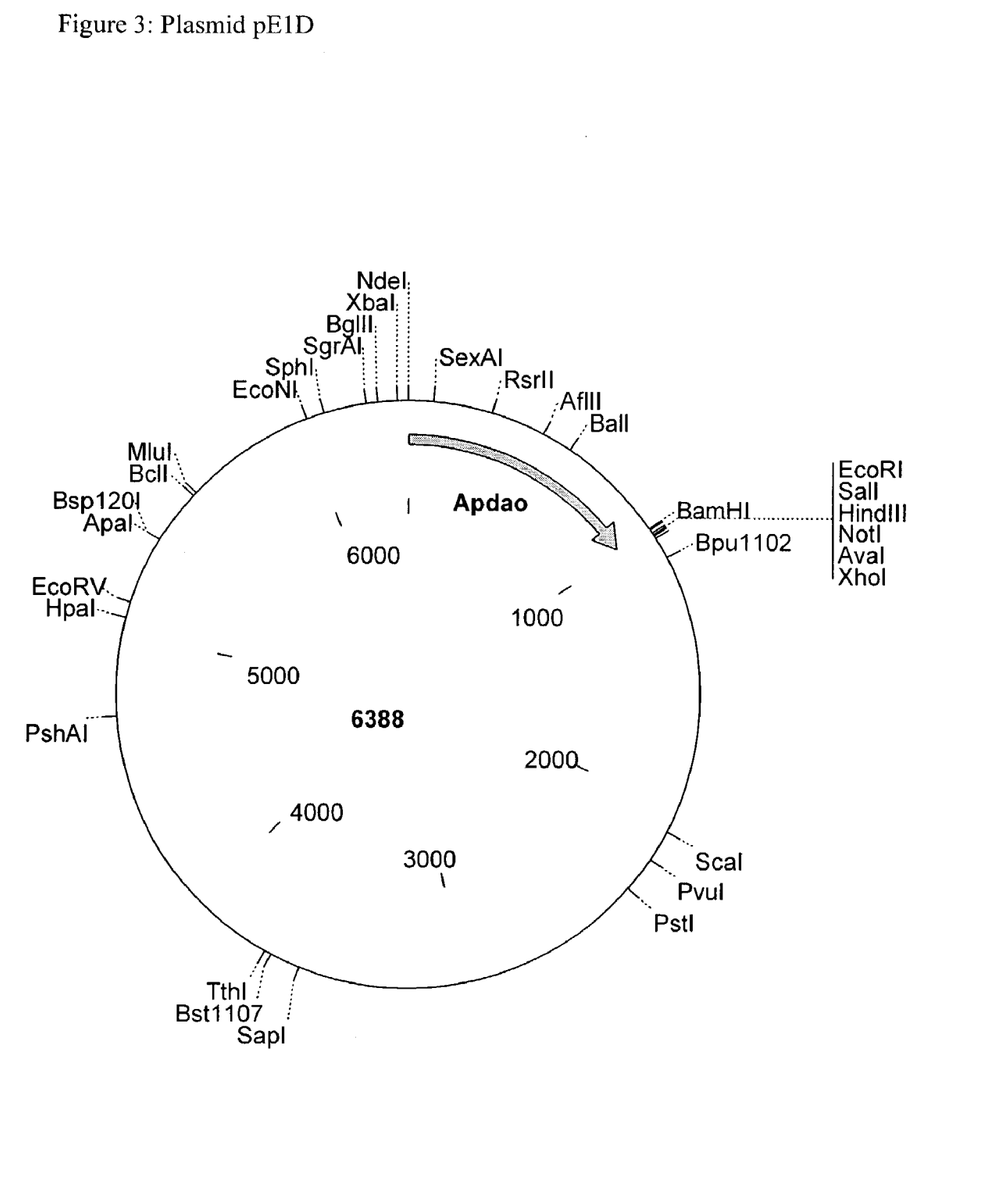
FIG. 3: Plasmid pE1D.
Figure 4:
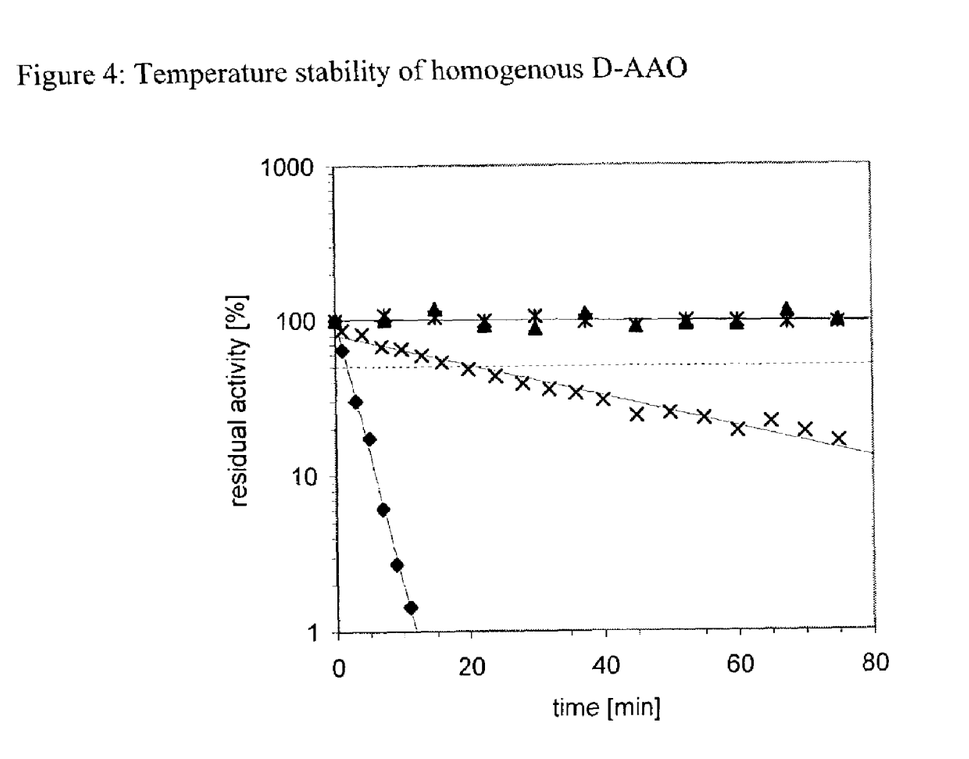
FIG. 4: Temperature stability of homogenous D-AAO: The enzyme was incubated at four different temperatures (▲ 20° C.; * 30° C.; X 40° C.; ♦ 50° C.). Residual activity was measured under standard assay conditions.

The restriction sites NdeI and BamHI were attached to the dao gene by PCR. The PCR product was digested and ligated into pET21a (available from Novagen) to give pE1D (see FIG. 3). This DNA was transformed into *E. coli* XL1 blue and BL21(DE3). *E. coli* BL21(DE3) carrying the plasmid pE1D was cultivated aerobically in 100 ml-shaking flasks containing 20 ml Luria-Bertani medium and 100 µg/ml ampicillin. The cells were incubated at 37° C. and 200 rpm. They were induced with 100 µM IPTG when they reached an optical density of $OD_{550}$~0.5. After induction, the tem perature was reduced to 30° C. and the cells were incubated for 4 more hours. The specific D-AAO activity in the crude extract reached 30 U/mg.

All references cited herein are fully incorporated by reference. Having now fully described the invention, it will be understood by one of ordinary skill in the art that the invention may be performed within a wide and equivalent range of conditions, parameters and the like, without affecting the spirit or scope of the invention or any embodiment thereof.

---

What is claimed is:

1. An isolated protein comprising the amino acid sequence of SEQ ID NO:2, wherein said protein has D-amino acid oxidase activity.

2. An isolated protein consisting of the amino acid sequence of SEQ ID NO:2.

3. A composition comprising the isolated protein of claim 1, and at least one amino acid selected from the group consisting of D-methionine; D-lysine; D-phenylalanine; 4-fluoro-DL-phenylalanine; DL-Homophenylalanine; and D-arginine.

4. The composition of claim 3, wherein said amino acid is D-methionine.

5. The composition of claim 3, wherein said amino acid is D-lysine.

6. The composition of any one of claims 3–5, further comprising the cofactor flavin adenine dinucleotide (FAD).

7. A composition comprising the isolated protein of claim 2, and at least one amino acid selected from the group consisting of: D-methionine; D-lysine; D-phenylalanine; 4-fluoro-DL-phenylalanine; DL-Homophenylalanine; and D-arginine.

8. The composition of claim 7, wherein said amino acid is D-methionine.

9. The composition of claim 7, wherein said amino acid is D-lysine.

10. The composition of any one of claim 9, further comprising the cofactor FAD.

11. The protein of either claim 1 or claim 2, wherein said protein is immobilized.

12. The protein of claim 11, wherein said protein is immobilized by lyophilization in the presence of a surface-active substance.

13. The protein of claim 12, wherein said surface-active substance is selected from the group consisting of: Aerosol OT; polyvinylpyrrolidone; polyethylene glycol; and Brij 52.

14. A process for the oxidative deamination of D-amino acids comprising, contacting said amino acids with the protein of either claim 1 or claim 2 under suitable conditions for said oxidative deamination.

15. The process of claim 14, wherein said D-amino acids are basic amino acids and are converted into keto acids.

* * * * *

SEQUENCE LISTING

<160> NUMBER OF SEQ ID NOS: 8

<210> SEQ ID NO 1
<211> LENGTH: 981
<212> TYPE: DNA
<213> ORGANISM: Arthrobacter protophormiae

<400> SEQUENCE: 1

```
atgcccacag caccgttgag aatcaccgtg atcggttccg gcgtcatcgg cctgtccgcg    60
gcccacgagc tggccgccgc cgggcaccag gtcaccgtcg cctacgacca ggagctcgcc   120
gagtgcgtct cctcggtcgc cgccgccatc tggttcccgt accactcgga gaactccccg   180
gccgccgaca agctgctggc ggattcgctg gcccgcttcg agcagctgtc cgagcacccc   240
gaaaccggca tcgacctgcg ccgcggcttg aatgtggacc acctgccggg cgcggaccgc   300
agctggaccc gcatcgtcgc cggcaccgag gaagcctctc ccgcggatct gcggacggc    360 gcccacgcgg gcgtgtgggc gacggtgccg atcattacca tgagcaccta cctgggctgg   420
ctgcgcggcc gggtcgagga gctgggcgcg gacttcgcca agggcacggt cacggatctg   480
gcgcagctta agggcggcgc ggatctggtg gtgctggcag cgggcctgcg cggcggcgag   540
ctgctgggcg acgacgatac cgtctacccg atccgcgggc aggtggtgcg cctggccaac   600
acgaagaacc tgacgcagtg gctgtgcgac gacaactacc cggatggcgt cagctacatc   660
atcccccgcc gcgaggacat catcgtggga ggcaccgaca ccgcgaacga ctggaaccgc   720
gaagtcgaac cgcagacctc catcgacatc ctggaacgcg ctgccaagct ggtgccggag   780
ctggaaggac tggaggtcct ggagcacaag gtgggcctgc gcccggcgcg cgagaccatc   840
cggctggagc acgtcgcggg ccacccgctg ccggtgatcg ccgcctacgg cacggcggt    900 gccggcgtca cgctgtcctg gggcaccgca cagcgggtcg cagagctggc tgcacaactg   960
gctggcgagc cggccagcta g                                              981
```

<210> SEQ ID NO 2
<211> LENGTH: 326
<212> TYPE: PRT
<213> ORGANISM: Arthrobacter protophormiae

<400> SEQUENCE: 2

```
Met Pro Thr Ala Pro Leu Arg Ile Thr Val Ile Gly Ser Gly Val Ile
1               5                   10                  15

Gly Leu Ser Ala Ala His Glu Leu Ala Ala Ala Gly His Gln Val Thr
            20                  25                  30

Val Ala Tyr Asp Gln Glu Leu Ala Glu Cys Val Ser Ser Val Ala Ala
        35                  40                  45

Ala Ile Trp Phe Pro Tyr His Ser Glu Asn Ser Pro Ala Ala Asp Lys
    50                  55                  60

Leu Leu Ala Asp Ser Leu Ala Arg Phe Glu Gln Leu Ser Glu His Pro
65                  70                  75                  80

Glu Thr Gly Ile Asp Leu Arg Arg Gly Leu Asn Val Asp His Leu Pro
                85                  90                  95
```

```
Gly Ala Asp Arg Ser Trp Thr Arg Ile Val Ala Gly Thr Glu Glu Ala
            100                 105                 110

Ser Pro Ala Asp Leu Pro Asp Gly Ala His Ala Gly Val Trp Ala Thr
            115                 120                 125

Val Pro Ile Ile Thr Met Ser Thr Tyr Leu Gly Trp Leu Arg Gly Arg
130                 135                 140

Val Glu Glu Leu Gly Ala Asp Phe Ala Lys Gly Thr Val Thr Asp Leu
145                 150                 155                 160

Ala Gln Leu Lys Gly Gly Ala Asp Leu Val Val Leu Ala Ala Gly Leu
            165                 170                 175

Arg Gly Gly Glu Leu Leu Gly Asp Asp Asp Thr Val Tyr Pro Ile Arg
            180                 185                 190

Gly Gln Val Val Arg Leu Ala Asn Thr Lys Asn Leu Thr Gln Trp Leu
            195                 200                 205

Cys Asp Asp Asn Tyr Pro Asp Gly Val Ser Tyr Ile Ile Pro Arg Arg
            210                 215                 220

Glu Asp Ile Ile Val Gly Gly Thr Asp Thr Ala Asn Asp Trp Asn Arg
225                 230                 235                 240

Glu Val Glu Pro Gln Thr Ser Ile Asp Ile Leu Glu Arg Ala Ala Lys
            245                 250                 255

Leu Val Pro Glu Leu Glu Gly Leu Glu Val Leu Glu His Lys Val Gly
            260                 265                 270

Leu Arg Pro Ala Arg Glu Thr Ile Arg Leu Glu His Val Ala Gly His
            275                 280                 285

Pro Leu Pro Val Ile Ala Ala Tyr Gly His Gly Gly Ala Gly Val Thr
            290                 295                 300

Leu Ser Trp Gly Thr Ala Gln Arg Val Ala Glu Leu Ala Ala Gln Leu
305                 310                 315                 320

Ala Gly Glu Pro Ala Ser
            325

<210> SEQ ID NO 3
<211> LENGTH: 20
<212> TYPE: PRT
<213> ORGANISM: Arthrobacter protophormiae

<400> SEQUENCE: 3

Pro Thr Ala Pro Leu Arg Ile Thr Val Ile Gly Ser Gly Val Ile Gly
1               5                   10                  15

Leu Ser Ala Ala
            20

<210> SEQ ID NO 4
<211> LENGTH: 14
<212> TYPE: PRT
<213> ORGANISM: Arthrobacter protophormiae

<400> SEQUENCE: 4

Leu Val Pro Glu Leu Glu Gly Leu Glu Val Leu Glu His Lys
1               5                   10

<210> SEQ ID NO 5
<211> LENGTH: 27
<212> TYPE: DNA
<213> ORGANISM: Arthrobacter protophormiae

<400> SEQUENCE: 5
gcaccaggtc accgtcgcct acgacca                                      27
```

```
<210> SEQ ID NO 6
<211> LENGTH: 26
<212> TYPE: DNA
<213> ORGANISM: Arthrobacter protophormiae

<400> SEQUENCE: 6
caccagcttg gcagcgcgtt ccagga                                        26

<210> SEQ ID NO 7
<211> LENGTH: 27
<212> TYPE: DNA
<213> ORGANISM: Arthrobacter protophormiae

<400> SEQUENCE: 7
cgccgccgcc atctggttcc cgtacca                                       27

<210> SEQ ID NO 8
<211> LENGTH: 30
<212> TYPE: DNA
<213> ORGANISM: Arthrobacter protophormiae

<400> SEQUENCE: 8
ctgcggttcg acttcgcggt tccagtcgtt                                    30
```